(12) United States Patent
Tu et al.

(10) Patent No.: US 8,664,440 B2
(45) Date of Patent: Mar. 4, 2014

(54) METHOD FOR PREPARING ALISKIREN AND ITS INTERMEDIATES THEREOF

(75) Inventors: Yongjun Tu, Taizhou (CN); Yi Zhang, Taizhou (CN); Rongde Cheng, Taizhou (CN); Lingchao Peng, Taizhou (CN)

(73) Assignee: Zhejiang Tianyu Pharmaceutical Co., Ltd, Taizhou (CN)

( * ) Notice: Subject to any disclaimer, the term of this patent is extended or adjusted under 35 U.S.C. 154(b) by 0 days.

(21) Appl. No.: 13/639,144

(22) PCT Filed: Apr. 19, 2010

(86) PCT No.: PCT/CN2010/000526
§ 371 (c)(1),
(2), (4) Date: May 6, 2013

(87) PCT Pub. No.: WO2011/082506
PCT Pub. Date: Jul. 14, 2011

(65) Prior Publication Data
US 2013/0225841 A1    Aug. 29, 2013

(30) Foreign Application Priority Data
Jan. 6, 2010    (CN) .......................... 2010 1 0000057

(51) Int. Cl.
*A61K 31/16*    (2006.01)
*C07C 239/00*   (2006.01)

(52) U.S. Cl.
USPC ......................................... 564/157; 514/616

(58) Field of Classification Search
None
See application file for complete search history.

(56) References Cited

U.S. PATENT DOCUMENTS

2009/0076062 A1    3/2009 Maibaum et al.

FOREIGN PATENT DOCUMENTS

| WO | WO2006024501 | 3/2006 |
| WO | WO2007045420 | 4/2007 |

OTHER PUBLICATIONS

International Search Authority-PCT;English Translation of Written Opinion of Search Authority; Nov. 29, 2012.
PCT International Search Report.
International Search Report for PCT/CN2010/000526.

*Primary Examiner* — Janet L Andres
*Assistant Examiner* — Heidi Reese
(74) *Attorney, Agent, or Firm* — Stites & Harbison PLLC; Cong Ding

(57) ABSTRACT

A method for preparing Aliskiren and intermediate thereof, which comprises the following steps: reacting 4-bromo-1-methoxy-2-(3-methoxypropoxy)benzene with magnesium isopropyl chloride and n-BuLi to obtain the compound of formula XXII; reacting the product of methylsulfonylation of the compound of formula XIX with anhydrous LiBr to obtain the compound of formula XXI; obtaining the intermediate of Aliskiren shown as formula XV by reacting the compound of formula XXII with the compound of formula XXI in an ether as the solvent and in the presence of a catalyst containing iron; then reacting the compound of formula XV with the compound of formula VII to obtain the compound of formula XXIII, following removing $R^1$ from the amino group and obtaining Aliskiren shown as formula I.

14 Claims, No Drawings

METHOD FOR PREPARING ALISKIREN AND ITS INTERMEDIATES THEREOF

CROSS REFERENCE TO RELATED APPLICATIONS

This application is a §371 National State Application of PCT/CN2010/000526 filed Apr. 19, 2010, which claims priority to CN201010000057.3 filed Jan. 6, 2010.

FIELD OF THE INVENTION

The present invention is in the field of pharmaceutical preparation method. More particularly, it relates to a method of preparation for Aliskiren and its intermediates.

BACKGROUND OF THE INVENTION

Aliskiren (I) is a second generation renin inhibitor with renin-angiotensin system (RAS) as its target. It's used clinically in the form of Aliskiren hemifumarate (Rasilez®) and was approved by FDA in May, 2007.

Aliskiren has the chemical name: (2S,4S,5S,7S)-5-amino-N-(2-carbamoyl-2-methylpropyl)-4-hydroxy-2-isopropyl-7-[4-methoxy-3-(3-methoxypropoxy)benzyl]-8-methyloctanamide (CAS No.: 173334-57-1). Its chemical structure is illustrated with Formula I given below:

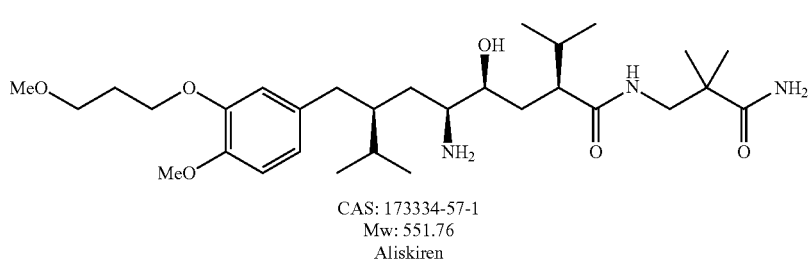

CAS: 173334-57-1
Mw: 551.76
Aliskiren

The method of preparation for Aliskiren and its intermediates has been reported in U.S. Pat. No. 7,132,569, WO0208172, U.S. Pat. No. 5,559,111, (equivalent patent to CN1266118), U.S. Pat. No. 5,606,078, CN01016253, WO2007/045421, EP2002874, Helvetica ChimicaActa (2005, 3263-13273).

In U.S. Pat. No. 7,132,569, WO0208172 et al., the preparation of Aliskiren (I) comprises the following steps as described in reaction scheme 1: coupling 2-(3-methoxypropoxy)-4-((R)-2-(bromomethyl)-3-methylbutyl)-1-methoxybenzene (II) with (2S,4E)-5-chloro-2-isopropyl-4-pentenoic acid derivative (III) to obtain the compound of formula IV; halolactonization of the compound of formula IV to obtain the compound of formula V; then substituting the compound of formula V with azide to obtain the compound of formula VI; ring-opening the compound of formula VI with 3-amino-2,2-dimethylpropionamide (VII) in the presence of 2-hydroxypyridine and triethylamine to obtain the compound of formula VIII and a final catalytic hydrogenation of the compound of formula VIII to obtain Aliskiren (I). This preparation process is illustrated in Reaction Scheme 1.

Reaction Scheme 1:

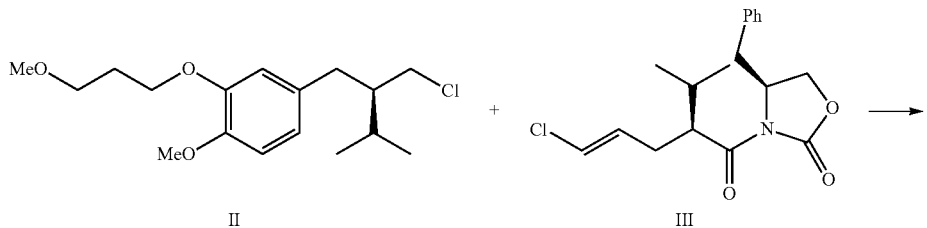

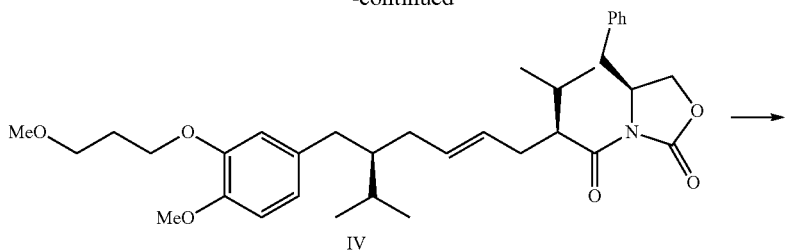

IV

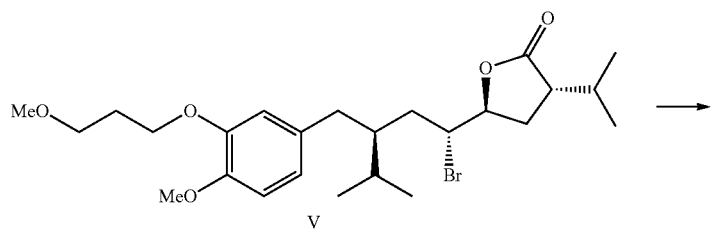

V

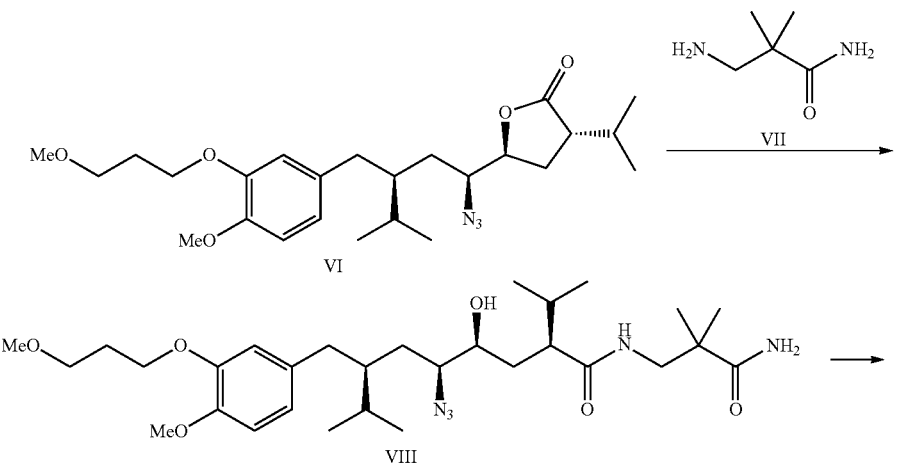

VI

VII

VIII

→ I

In the patented preparation described above, chiral starting materials with the compounds of formula II and III are utilized to obtain the compound of formula IV. However, the reactions followed after the preparation of the compound of formula IV, such as the halolactonization and especially the substitutive reaction between the compound of formula V and azide, have problems of low yields and numerous by-products, which is not conducive to industrial scale production.

U.S. Pat. No. 5,559,111 (equivalent patent CN1266118) and U.S. Pat. No. 5,606,078 et al. report the preparation of the compound of formula XI via Grignard reaction with 4-bromo-1-methoxy-2-(3-methoxypropoxy)benzene (IX) and the compound of formula X as starting materials as illustrated in Reaction Scheme 2:

Reaction Scheme 2:

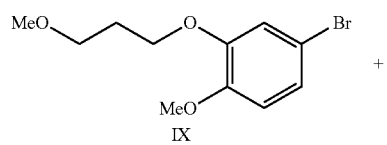

IX

+

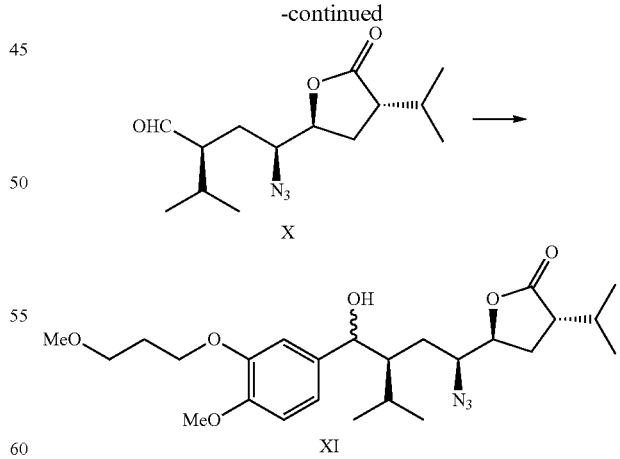

X

XI

In the patented preparation described above, there are multiple reaction steps in the preparation of the compound of formula X from the compound of formula XII. The key steps, as described in Reaction Scheme 3, involve selective reduction agents such as sodium tri-tert-butoxyaluminum hydride and diisobutylaluminium hydride to prepare aldehyde and the reaction conditions need to be very well-controlled.

Reaction Scheme 3:

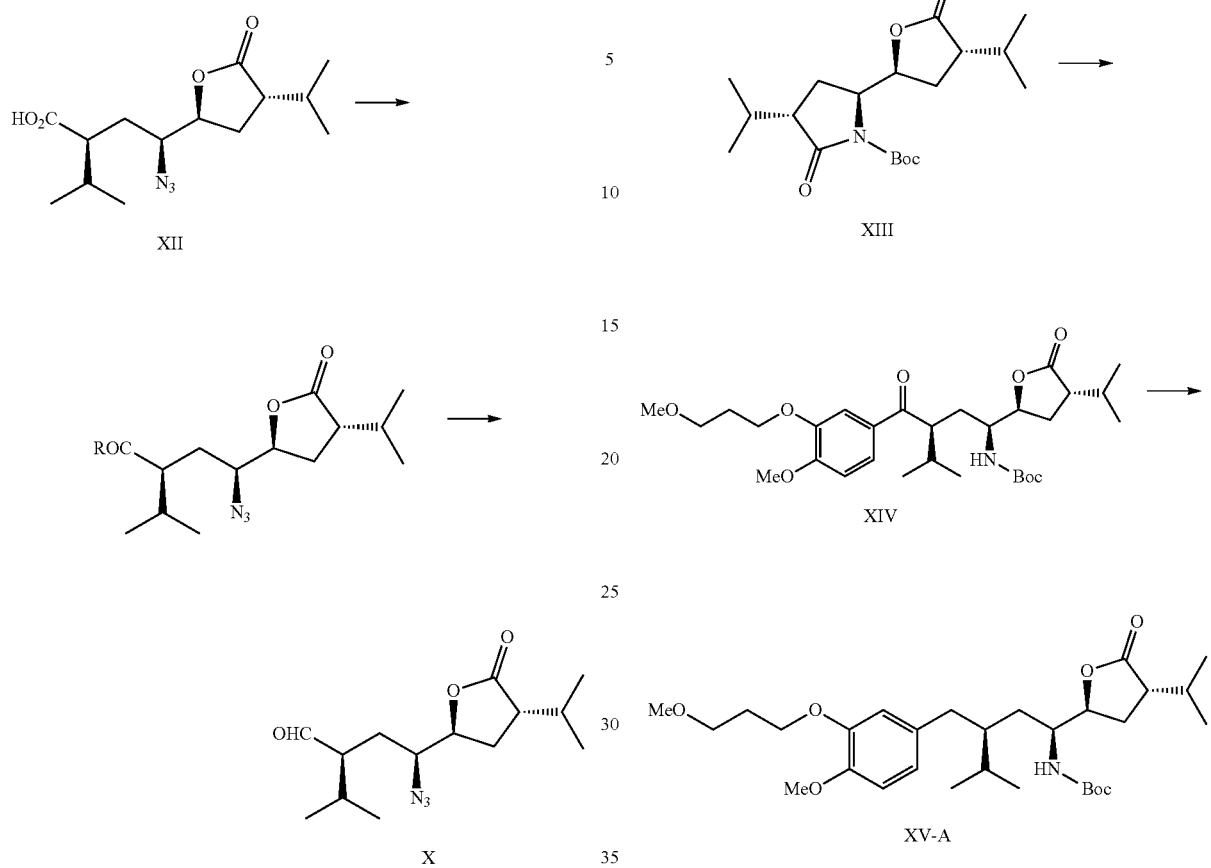

The compound of formula XI prepared by reaction scheme 2 could then be convened into Aliskiren (I) after multiple catalytic hydrogenation, protection and de-protection. In this method of preparation, a stepwise catalytic hydrogenation, azido reduction and dehydroxylation were implemented to reduce by-products during the catalytic hydrogenation. In addition, it is necessary to protect and de-protect the free hydroxyl group during the preparation. This synthetic scheme has disadvantage of multiple synthetic steps, tedious operation, lengthy overall reaction duration, low yield and particularly high production cost for the starting compound of formula X.

WO2007/045421 has reported an improved preparation method in which the starting material 4-bromo-1-methoxy-2-(3-methoxypropoxy)benzene (IX) firstly reacts with the compound of formula XIII via Grignard reaction to obtain the compound of formula XIV, and then followed by catalytic hydrogenation and ketone reduction to yield the compound of formula XV-A, as illustrated in Reaction Scheme 4:

Reaction Scheme 4:

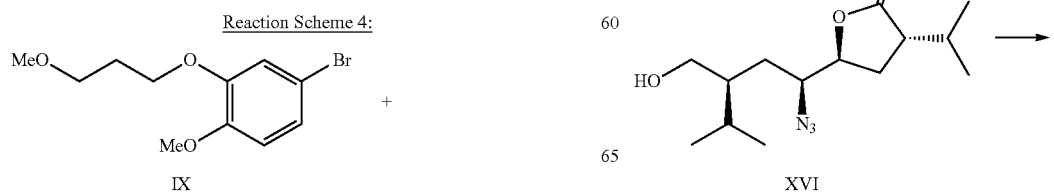

In the above preparation, expensive reagents, such as sodium tri-tert-butoxyaluminum hydride and diisobutylaluminium hydride were eliminated, but additional synthetic steps were introduced. In addition, the preparation of the compound of formula XV-A prepared from the compound of formula XIV via ketone reduction required extended reaction time, great amount of catalyst with multiple small addition and good operation skills.

EP2062874A1 provides a method in preparing the compound of formula XVI. In this method, the compound of formula XVII is obtained from the compound of formula XVI via halogenation. A corresponding Grignard reagent is firstly prepared from the compound of formula IX or XVII reacting with magnesium, which is then couples with another chemical in the presence of the metal catalyst iron(III) acetylacetonate (Fe(acac)3) to obtain the compound of formula XVIII as described in Reaction Scheme 5:

Reaction Scheme 5:

-continued

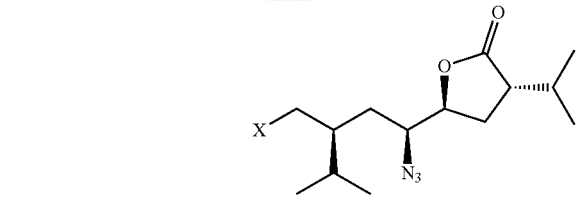

XVII

X = Cl, Br

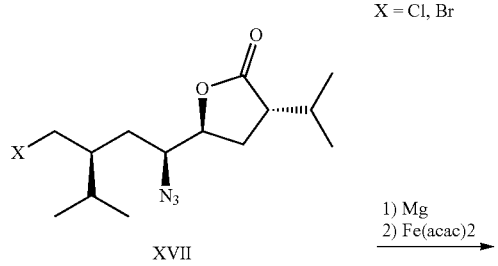

XVII

X = Cl, Br

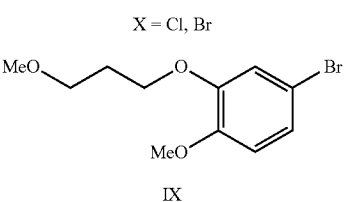

IX

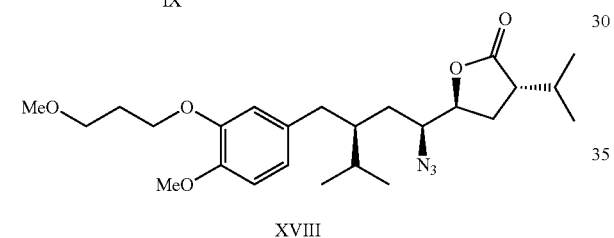

XVIII

In EP2062874A1, the compound of formula XVIII reacts with 3-amino-2,2-dimethylpropionamide (VII). The resulted product is then through reduction of the azio group to obtain Aliskiren (I). In this patent, detailed experimental protocol was not provided although N-methylpyrrolidone was mentioned as solvent. We found: 1) it is difficult to prepare the Grgnard reagent from the compound of formula IX; 2) the compounds of formula XVII and XVIII are not quite stable in the presence of iron(III) acetylacetonate. In addition, the yield in preparing the compound of formula XVIII was extremely low.

In summary, there are disadvantage among the current available methods in preparing Aliskiren, such as expensive starting materials, complicated reaction operations, difficulties in controlling by-products and lengthy reaction time. Therefore, its necessary and technically meaningful to develop a novel method for Aliskiren and its intermediates preparation to avoid current disadvantage.

SUMMARY OF THE INVENTION

The present invention provides a novel method for preparing Aliskiren and its intermediates to overcome the disadvantages in the current existing methods which are high cost in starting materials, complicated reaction operations, difficulties in controlling by-products and lengthy reaction time.

The present invention with the technical embodiment below:

A method for preparing Aliskiren intermediate with the compound of formula XV comprises the following steps:

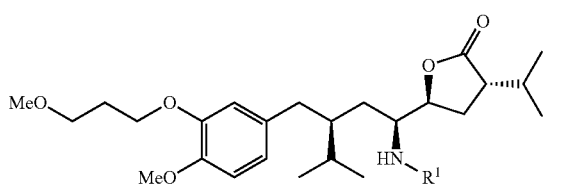

XV (1). reacting the compound of formula IX 4-bromo-1-methoxy-2-(3-methoxypropoxy)benzene with sequentially added isopropylmagnesium chloride and n-butyllithium in an ether class solvent under temperature of −25° C.~20° C. to obtain the intermediate as illustrated in compound of formula XXII;

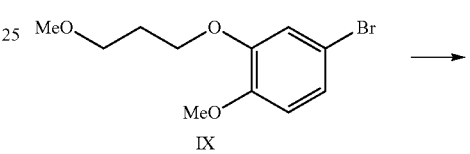

IX

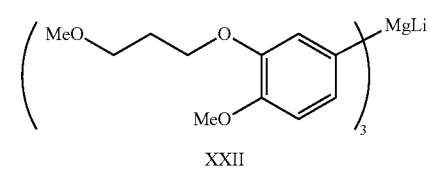

XXII (2). methylsulfonylation of the compound of formula XIX in an inert solvent under temperature of −10° C.~25° C. to obtain the compound of formula XX as illustrated, where Ms is methylsulfonyl group;

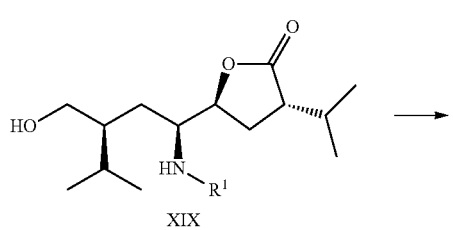

XIX

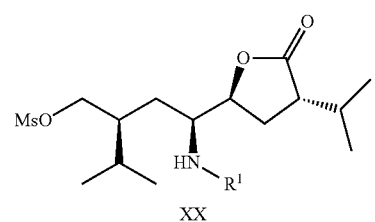

XX (3). substituting the intermediate compound of formula XX with anhydrous lithium bromide in a ketone class solvent under temperature of 35° C. to refluxing temperature to obtain the intermediate compound of formula XXI as shown;

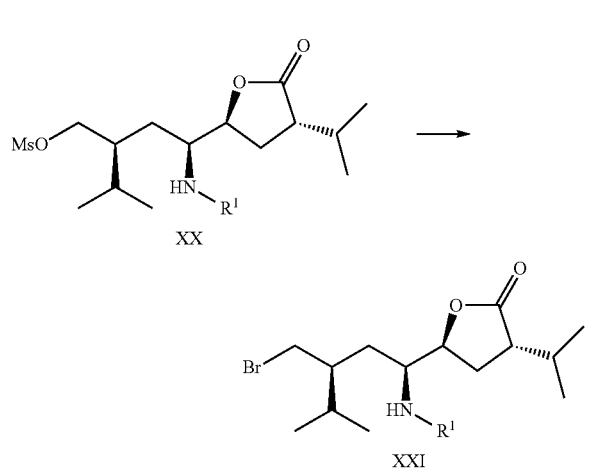

(4). coupling the intermediate compound of formula XXII in step (1) with the intermediate compound of formula XXI in step (3) in an ether class solvent under temperature of −25° C.~55° C. in the presence of iron-contained catalyst to obtain the compound of formula XV;

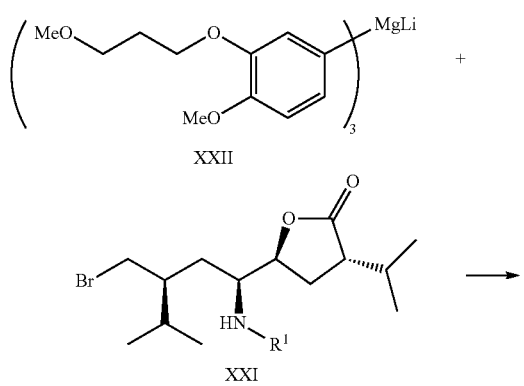

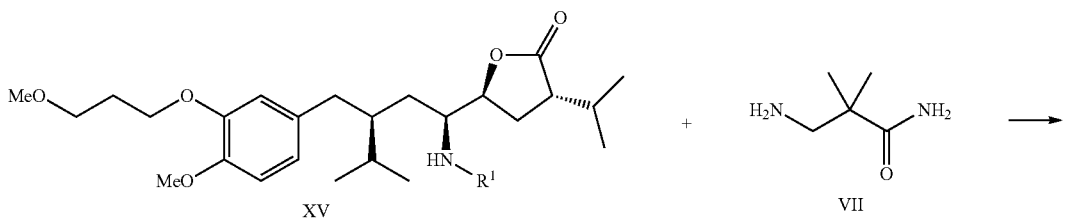

wherein $R^1$ is $^{tert}$butoxycarbonyl or benzyloxycarbonyl group in the compounds of formula XV, XIX, XX and XXI in the above reaction steps.

The above technical embodiment for preparing the Aliskiren intermediate compound of formula XV, wherein the ether class solvent employed in solubilizing 4-bromo-1-methoxy-2-(3-methoxypropoxy)benzene in step (1) is selected from diethyl ether, tetrahydrofuran or 1,2-dimethoxyethane.

The above technical embodiment for preparing the Aliskiren intermediate compound of formula XV, wherein the inert solvent employed in step (2) is methylene chloride or tetrahydrofuran.

The above technical embodiment for preparing the Aliskiren intermediate compound of formula XV, wherein the said ketone class solvent is acetone or 2-butanone in step (3), and the molar ratio between lithium bromide and the compound of formula XX is 1.1 to 5.

The above technical embodiment for preparing the Aliskiren intermediate compound of formula XV, wherein the ether class solvent employed in step (4) is either one or a mixture of any two of diethyl ether, tetrahydrofuran or 1,2-dimethoxyethane; the iron-contained catalyst is iron(III) acetylacetonate or Iron(III) chloride; the reaction temperature is −25° C.~55° C., the preferred temperature is −15° C.~20° C., and yet the particularly preferred temperature is 0° C.~20° C.

Another technical embodiment shows a method for preparing the Aliskiren compound of formula I, wherein said method for preparing the Aliskiren compound of formula I comprises the method for preparing the Aliskiren intermediate compound of formula XV as described above, further comprises the following steps:

(a). reacting the compound of formula XV with the compound of formula VII, as both prepared from the above technical embodiment, in the presence of 2-hydroxypyridine and triethylamine to obtain the compound of formula XXIII;

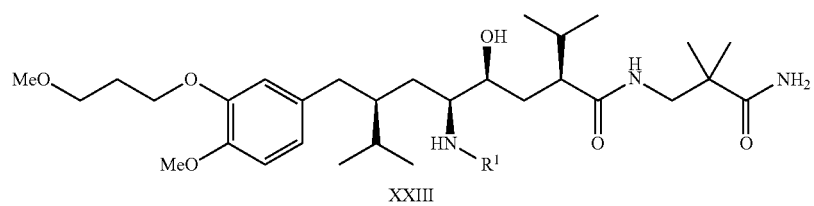

(b). removing the $R^1$ group on the amino group in the compound of formula XXIII to obtain the Aliskiren compound of formula I;

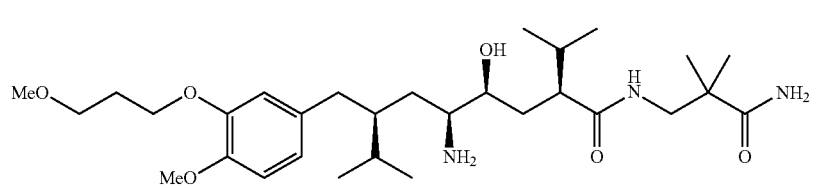

wherein the $R^1$ is $^{tert}$butoxycarbonyl or benzyloxycarbonyl group in the compounds of formula XV and XXIII.

The above method in preparing the Aliskiren compound of formula I, wherein the reaction in step (a) for preparing the compound of formula XXIII from the compound of formula XV and the compound of formula VII is performed in an inert solvent.

The above method for preparing the Aliskiren compound of formula I, wherein the inert solvent is dioxane or toluene.

The above method for preparing the Aliskiren compound of formula I, wherein the acidic de-alkylation to remove $R^1$ group is performed under −25° C.~0° C. with the acid selected among, trifluoroacetic acid, hydrochloride and concentrated sulfuric acid when $R^1$ is $^{tert}$butoxycarbonyl group, and the preferred reaction temperature is −20° C.~−5° C., and yet the particularly preferred reaction temperature is −15° C.~−10° C.

The above method for preparing the Aliskiren compound of formula I, when said $R^1$ is benzyloxycarbonyl group, the catalytic hydrogenation to remove $R^1$ group is performed in the presence of Pd—C catalyst under temperature of 20° C.~60° C. and atmospheric pressure of 1 to 10 atm; the preferred reaction conditions are 25° C.~45° C. and 2 to 7 atm; and yet the particularly preferred reaction conditions are 30° C.~40° C. and 4 to 6 atm.

The present invention provides the below advantages:

1. Compared to the current reported methods which have disadvantages such as instabilities of the compounds of formula XVIII and XVIII in the presence of iron(III) acetylacetonate and extreme low yield in preparing the target compound of formula XVIII from the compound of formula XVIII and the Grignard reagent from the compound of formula IX and magnesium, in the present invention, the compound of formula IX first reacts with isopropylmagnesium chloride and n-butyllithium to obtain the aromatic magnesiumlithium compound of formula XXII; then the resulted aromatic magnesiumlithium compound of formula XXII reacts with the compound of formula XXI under mild condition by following the protocol in step (4) to obtain the compound of formula XV.

2. Compared to the current reported methods in preparing Aliskiren, the present invention has advantages of low starting material cost, simple synthetic protocol and easy preparation for industrialization.

DESCRIPTION OF THE SPECIFIC PREFERRED EMBODIMENTS

To better elucidate the technical method in the present invention, detailed examples are given below to further explain the present invention. The yields are molar yields in the following examples.

Example 1

Preparation of the Intermediate {(1S,3S)-1-((2S,4S)-4-isopropyl-5-oxo-furanidin-2-yl)-3-[4-methoxy-3-(3-methoxy-propoxy)-benzyl]-4-methyl-pentyl}-carbamic acid tert-butyl ester (XV-A)

[Step 1]: preparation of [(1S,3S)-3-hydroxymethyl-1-((2S,4S)-4-isopropyl-5-oxo-furanidin-2-yl)-4-methyl-pentyl]-carbamic acid tert-butyl ester (XIX-A): The synthetic method in U.S. Pat. No. 5,606,078 example 7 is followed.

[Step 2]: Preparation of [(1S3S)-3-bromomethyl-1-((2S,4S)-4-isopropyl-5-oxo-furanidin-2-yl)-4-methyl-pentyl]-carbamic acid tert-butyl ester (XXI-A):

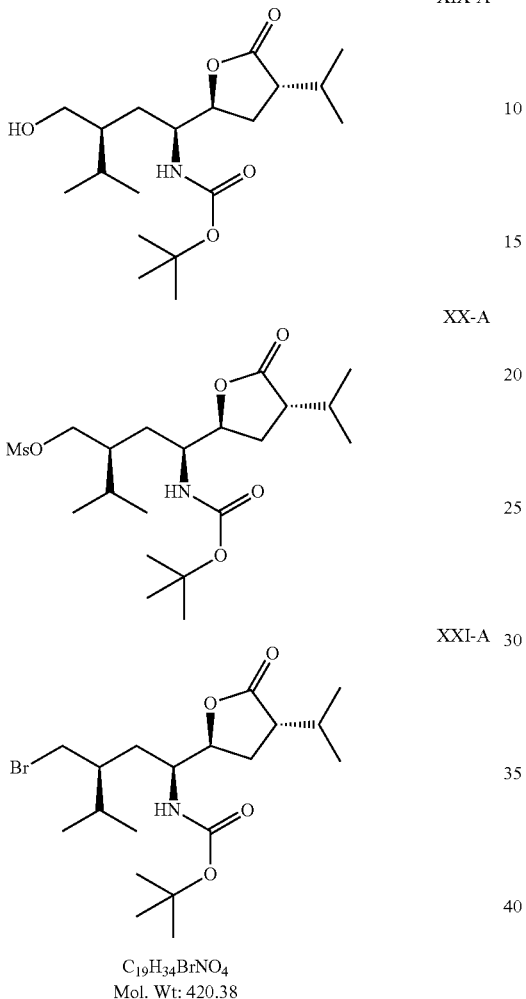

XIX-A

XX-A

XXI-A $C_{19}H_{34}BrNO_4$
Mol. Wt: 420.38

Under nitrogen protection, in a 250 ml round bottom flask equipped with constant pressure funnel, mechanical stirrer and thermometer, [(1S,3S)-3-hydroxymethyl-1-((2S,4S)-4-isopropyl-5-oxo-furanidin-2-yl)-4-methyl-pentyl]-carbamic acid tert-butyl ester (the compound of formula XIX-A) (25.0 g, 70 mmol), triethylamine (9.2 g, 91 mmol) and methylene chloride (135 ml) are sequentially added and dissolved wider stirring. The reaction mixture is cooled down to 0-5° C. with an ice-water bath. Methanesulfonyl chloride (8.8 g 77 mmol) is added slowly under such temperature and the reaction is allowed to continue for another hour; then the ice-water bath is removed and the reaction temperature is increased to room temperature. After 4 additional hours, TLC monitoring demonstrates the starting materials are almost depleted. The reaction mixture is transferred into a separatory funnel with addition of deionized water (50 ml) and is allowed to develop into water phase and organic phase; the water phase is extracted with methylene chloride (30 ml) twice. The organic phases are combined and washed with saturated saline (50 ml), deionized water (50 ml) and dried with anhydrous sodium sulfate. After filtration and removal of solvent under reduced pressure, the resulted residue is the compound of formula XX-A.

In a 250 ml round bottom flask equipped with reflux condenser (with drying tube at its end), mechanical stirrer and thermometer, the compound of formula XX-A prepared in the previous step, powder anhydrous lithium bromide (15.2 g, 175 mmol) and acetone (120 ml) are sequentially introduced. The reaction is heated to refluxing temperature under stirring and the TLC monitoring demonstrates the disappearance of starting materials after 15 hours. The reaction is cooled down and the solvent is removed under reduced pressure. The residue is dissolved in methylene chloride (100 ml) and deionized water (50 ml) and the mixture is allowed to develop into water phase and organic phase; the water phase is extracted with methylene chloride (30 ml) once and the organic phases are combined and sequentially washed with saturated saline (30 ml), deionized water (30 ml) and dried with anhydrous sodium sulfate. After filtration and removal of solvent under reduced pressure, the residue is purified with short column of silica gel chromatography to obtain the compound of formula XXI-A (26.8 g, overall two step yield of 91%) as a wax material. The compound of formula XXI-A can be characterized by data collected front MS m/z: 421.1 $(M+H)^+$; 1H NMR (400 MHz, CDCl3) δ 4.50-4.45 (m, 1H), 3.87 (m, 1H), 3.64-3.48 (m, 2H), 2.71-2.60 (m, 1H), 2.23-2.15 (m, 3H), 1.89-1.80 (m, 2H), 1.64-1.53 (m, 2H), 1.43 (s, 9H), 1.06 (d, J=7.2 Hz, 3H), 0.99-0.91 (m, 9H) ppm.

[Step 3]: preparation of {(1S,3S)-1-((2S,4S)-4-isopropyl-5-oxo-furanidin-2-yl)-3-[4-methoxy-3-(3-methoxy-propoxy)-benzyl]-4-methyl-pentyl}-carbamic acid tert-butyl ester (XV-A)

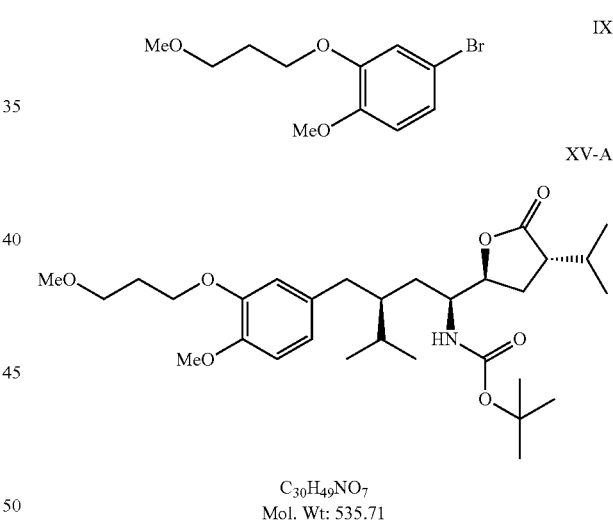

IX

XV-A $C_{30}H_{49}NO_7$
Mol. Wt: 535.71

Under nitrogen protection, a 150 ml reaction bottle is charged with 4-bromo-1-methoxy-2-(3-methoxypropoxy) benzene (the compound of formula IX) (8.3 g, 30 mmol) and anhydrous tetrahydrofuran (60 ml). The reaction is stirred for 10 minutes in an ice-water bath, followed by slow addition of isopropylmagnesium chloride in tetrahydrofuran (6.8 ml, 1.5 mol/L). The reaction is then stirred for another 15 minutes followed by addition of n-butyllithium in hexane (8.0 ml, 2.5 mol/L). After reacting for 4 more hours, the resulted aromatic magnesiumlithium compound of formula XXII is added direct into the next reaction step.

Under nitrogen protection, a 250 ml reaction bottle is charged with [(1S,3S)-3-bromomethyl-1-((2S,4S)-4-isopropyl-5-oxo-furanidin-2-yl)-4-methyl-pentyl]-carbamic acid tert-butyl ester (the compound of formula XXI-A) (8.4 g, 20 mmol) and iron(III) acetylacetonate (356 mg, 1 mmol). After nitrogen replacement for 2 times, anhydrous tetrahydrofuran (60 ml) is added and the reaction mixture is dissolved wider stirring. The reaction mixture is cooled down to −20° C. and the compound of formula XXII prepared from the previous reaction is added slowly. After addition, the reaction is maintained under the temperature for 3 hours and then reaction is allowed to reach room temperature and stirred for overnight. TLC monitoring demonstrates the starting materials are almost depleted. The reaction is then quenched with saturated ammonium chloride (50 ml) under an ice-water bath and the solvent is removed under reduced pressure. The residue is extracted with ethyl acetate (100 ml) twice and the combined organic phases are washed with saturated saline (30 ml), deionized water (30 ml) and dried with anhydrous sodium sulfate. After removal of solvent under reduced pressure, the residue is purified with short column of silica gel chromatography to obtain the compound of formula XV-A 8.1 g. The yield is 75% which is calculated from the compound of formula XXI-A.

The compound of formula XV-A can be characterized by data collected from: mp: 77-78° C.; MS (m/z): 536.3 (M+H)$^+$; $^1$H-NMR (400 MHz, CDCl3): δ 6.71 (d, 1H), 6.70 (s, 1H), 6.63 (d, J=8.1 Hz, 1H), 4.37-4.29 (m, 2H), 4.05 (t, J=6.3 Hz, 2H), 3.83-3.72 (m, 4H), 3.52 (t, J=6.3 Hz, 2H), 3.3 (S, 3H), 2.60-2.52 (m, 1H), 2.53-2.47 (m, 1H), 2.51-2.39 (m, 1H), 2.21-1.99 (m, 5H), 1.67-1.53 (m, 2H), 1.41 (s, 9H), 1.25-1.17 (m, 1H), 0.96-0.98 (d, 3H), 0.89 (d, 3H), 0.81-0.76 (m, 6H) ppm.

Example 2

Preparation of the Intermediate {(1S,3S)-1-((2S,4S)-4-isopropyl-5-oxo-furanidin-2-yl)-3-[4-methoxy-3-(3-methoxy-propoxy)-benzyl]-4-methyl-pentyl}-carbamic acid tert-butyl ester (XV-A)

The protocol in Example 2 is same to the protocol listed in Example 1 with the exceptions below. Tetrahydrofuran, instead, of methylene chloride, is used as solvent in the preparation of the compound of formula XX-A from the compound of formula XIX-A in [Step 2] of this example. Ethyl ether, instead of tetrahydrofuran, is used as solvent in the preparation of the compound of formula XXIII from the compound of formula XXI-A in [Step 3] of this example. Mixture of Ethyl ether and tetrahydrofuran, instead of tetrahydrofuran, is used as solvent in the preparation of the compound of formula XV-A from the compound of formula XXI-A and the compound of formula XXII.

Example 3

Preparation of the Intermediate {(1S,3S)-1-((2S,4S)-4-isopropyl-5oxo-furanidin-2-yl)-3-[4-methoxy-3-(3-methoxy-propoxy)-benzyl]-4-methyl-pentyl}-carbamic acid benzyl ester (XV-B)

[Step 1]: Preparation of [(1S,3 S)-3-hydroxymethyl-1-((2S,4S)-4-isopropyl-5-oxo-furanidin-2-yl)-4-methyl-pentyl]-carbamic acid benzyl ester (XIX-B):

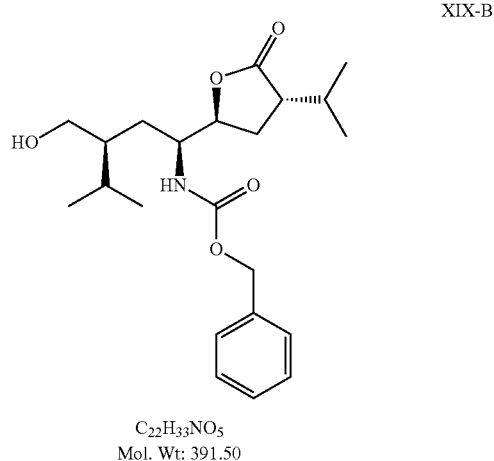 [SMILES: CC(C)[C@@H](CO)C[C@H](NC(=O)OCc1ccccc1)[C@@H]1C[C@@H](C(C)C)C(=O)O1]

XIX-B $C_{22}H_{33}NO_5$
Mol. Wt: 391.50

The similar synthetic method in U.S. Pat. No. 5,606,078 example 6 is followed with the only exception that chloroformic acid benzyl ester (17.1 g) is used to replace di-tert-butyl dicarbonate (Boc anhydride, 21.0 g) in preparing the [(1S,3S)-3-hydroxymethyl-1-((2S,4S)-4-isopropyl-5-oxo-furanidin-2-yl)-4-methyl-pentyl]-carbamic acid benzyl ester compound of formula (XIX-B) (29.2 g, yield of 86%). All other conditions remain the same.

The compound of formula XIX-B can be characterized by data collected from: mp: 117-119° C.; MS (m/z): 392.3 (M+H)$^+$; $^1$H-NMR (400 MHz, CDCl3): δ 7.25-7.16 (m, 5H), 5.4 (m, 1H), 5.2 (m, 1H), 4.62-4.45 (m, 2H), 3.87 (m, 1H), 3.65 (m, 1H), 3.66 (m, 1H), 2.51 (m, 1H), 2.31-2.15 (m, 3H), 2.03 (m, 1H), 1.81 (m, 1H), 1.75-1.34 (m, 3H), 1.15 (d, J=6.7 Hz, 3H), 0.98 (d, J=6.9 Hz, 3H), 0.90 (d, J=6.7 Hz, 3H), 0.81 (d, J=6.8 Hz, 3H) ppm.

[Step 2]: Preparation of [(1S,3S)-3-bromomethyl-1-((2S,4S)-4-isopropyl-5-oxo-furanidin-2-yl)-4-methyl-pentyl]-carbamic acid benzyl ester (XXI-B):

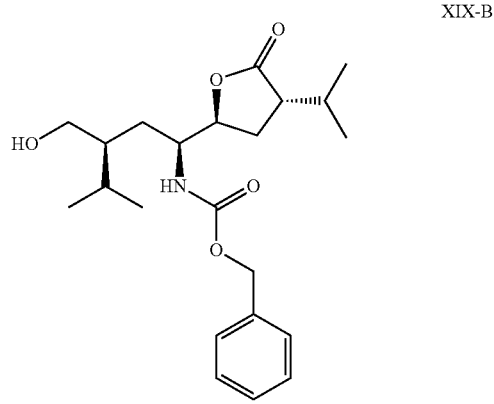

XIX-B

XXI-B

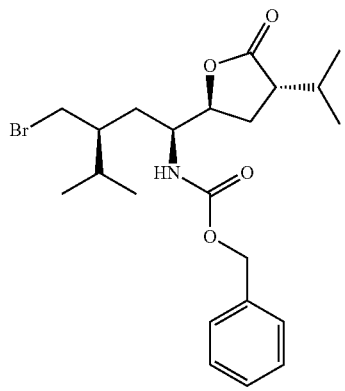

C<sub>22</sub>H<sub>32</sub>BrNO<sub>4</sub>
Mol. Wt: 454.40

The same method as described in in [Step 2] of Example 1 except using the [(1S,3S)-3-hydroxymethyl-1-((2S,4S)-4-isopropyl-5-oxo-furanidin-2-yl)-4-methyl-pentyl]-carbamic acid benzyl ester (the compound of formula XIX-B) (27.4 g, 70 mmol) to replace the compound of formula XIX-A, and buta one (110 ml) to replace acetone to obtain the target compound of formula XXI-B (28.6 g, 2 step overall yield of 89%) as a wax material. All other conditions are remained same.

The compound of formula XXI-B can be characterized by data collected from: MS (m/z): 455.1 (M+H)$^+$; $^1$H-NMR (400 MHz, CDCl3): δ 7.24-7.11 (m, 5H), 5.43 (m, 1H), 5.22 (m, 1H), 4.53-4.48 (m, 1H), 4.05-3.90 (m, 1H), 3.75-3.58 (m, 2H), 2.75-2.63 (m, 1H), 2.45-2.22 (m, 3H), 1.95-1.86 (m 2H), 1.67-1.58 (m, 2H), 1.07 (d, J=7.2 Hz, 3H), 0.99 (d, J=6.8 Hz, 3H), 0.97-0.89 (m, 6H) ppm.

[Step 3]: Preparation of {(1S,3S)-1-((2S,4S)-4-isopropyl-5-oxo-furanidin-2-yl)-3-[4-methoxy-3-(3-methoxy-propoxy)-benzyl]-4-methyl-pentyl}-carbamic acid benzyl ester (XV-B):

XV-B

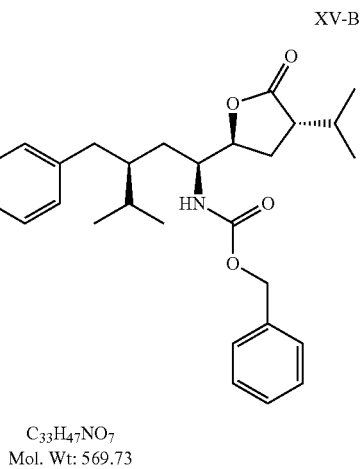

C<sub>33</sub>H<sub>47</sub>NO<sub>7</sub>
Mol. Wt: 569.73

Under nitrogen protection, a 150 ml reaction bottle is added with 4-bromo-1-methoxy-2-(3-methoxypropoxy)benzene (the compound of formula IX) (8.3 g, 30 mmol) and anhydrous tetrahydrofuran (60 ml). The reaction mixture is stirred for 10 minutes in an ice-water bath, then isopropylmagnesium chloride tetrahydrofuran solution (6.8 ml, 1.5 mol/L) is introduced slowly. The reaction is stirred for an additional 15 minutes and n-butyllithium n-hexane solution (8.0 ml, 2.5 mol/L) is added followed by maintaining the reaction for additional 4 hours to obtain the aromatic magnesiumlithium compound of formula XXII which is used directly in the next step reaction.

Under nitrogen protection, a 250 ml reaction bottle is charged with [(1S,3S)-3-bromomethyl-1-((2S,4S)-4-isopropyl-5-oxo-furanidin-2-yl)-4-methyl-pentyl]-carbamic acid benzyl ester (the compound of formula XXI-B) (8.2 g, 18 mmol) and iron(III) chloride (240 mg, 1.5 mmol). After nitrogen replacement for 2 times, anhydrous 1,2-dimethoxyethane (50 ml) is added and the reaction mixture is dissolved under stirring. The reaction mixture is cooled down to −15° C. and the compound of formula XXIII prepared from the previous step is added slowly. After addition, the reaction is maintained under the temperature for 1 hour and then reaction is allowed to reach room temperature slowly and stirred for overnight. TLC monitoring demonstrated the starting materials are almost depleted. The reaction is then quenched with saturated ammonium chloride (50 ml) under an ice-water bath and the solvent is removed under reduced pressure. The residue is extracted with ethyl acetate (100 ml) twice and the combined organic phases are washed with saturated saline (30 ml), deionized water (30 ml) and dried with anhydrous sodium sulfate. After removal of solvent under reduced pressure, the residue is purified with short column of silica gel chromatography to obtain the compound of formula XV-A 5.6 g as a wax material. The yield was 55% as calculated from the compound of formula XXI-B.

The compound of formula XV-A can be characterized by data collected from: MS (m/z): 570.4 (M+H)$^+$; $^1$H-NMR (400 MHz, DMSO): δ 7.25-7.14 (m, 5H), 6.87 (d, 1H), 6.77 (d, 1H), 6.71 (s, 1H), 6.71 (d, 1H), 5.41 (m, 1H), 5.21 (m, 1H), 4.35 (m, 2H), 3.92 (t, 2H), 3.78-3.57 (m, 3H), 3.45 (t, 2H), 3.35 (s, 3H), 2.72-2.61 (m, 1H), 2.51-2.45 (m, 1H), 2.32-2.22 (m, 1H), 1.85-2.10 (m, 5H), 1.57-1.50 (m, 2H), 1.23-1.10 (m, 1H), 1.01 (d, 3H), 0.90 (d, 3H), 0.81 (m, 6H) ppm.

Example 4

Preparation of Aliskiren

[Step 1]: Preparation of (1S,2S,4S)-4-(2-carbamoyl-2-methylpropyl-carbamoyl)-2-hydroxy-1-{(S)-2-[4-methoxy-3-(3-methoxypropoxy)-benzyl]-3-methylbutyl}-5-methyl-hexyl)-carbamic acid tert-butyl ester (XXIII-A):

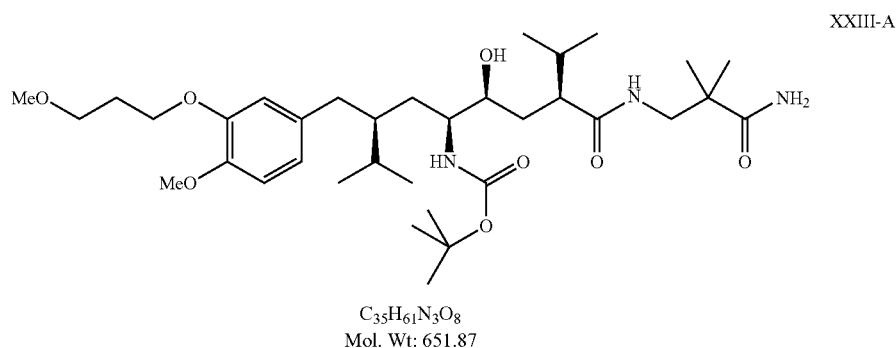 [SMILES: COCCCOc1cc(C[C@@H](C[C@H](NC(=O)OC(C)(C)C)[C@@H](O)C[C@H](C(=O)NCC(C)(C)C(N)=O)C(C)C)C(C)C)ccc1OC]

XXIII-A $C_{35}H_{61}N_3O_8$
Mol. Wt: 651.87

Under nitrogen protection, {(1S,3S)-1-(2S,4S)-4-isopropyl-5-oxo-furanidin-2-yl)-3-[4-methoxy-3-(3-methoxy-propoxy)-benzyl]-4-methyl-pentyl}-carbamic acid tert-butyl ester (the compound of formula XV-A) (5.4 g, 10 mmol) 2-hydroxypyridine (4.8 g, 5 mmol) and triethylamine (20 ml) are added sequentially into a 50 ml reaction bottle. After reaction mixture is dissolved under stirring, 3-amino-2,2-dimethylpropionamide (the compound of formula VII) (1.6 g, 14 mmol) is added and the reaction is warmed up to 80° C. for 18 hours. After TLC monitoring indicates the starting materials are almost completely exhausted, the volume of the reaction mixture is minimized by distillation under reduced pressure. The resulted residue is cooled down and re-dissolved in ethyl acetate (100 ml) and then sequentially washed with saturated saline (30 ml), deionized water (30 ml) and dried with anhydrous sodium sulfate. After filtration and removal of solvent under reduced pressure, the residue is purified with short column of silica gel chromatography to obtain the compound of formula XXIII-A (5.1 g) as a wax material. The yield is 78% as calculated from the compound of formula XV-A. The compound of formula XXIII-A can be characterized by data collected from; MS m/z: 652.6 (M+H)$^+$; 1H-NMR (400 MHz, CDCl$_3$) δ 6.76-6.67 (m, 3H), 6.55 (brs, 1H), 6.21 (brs, 1H), 5.82 (brs, 1H), 4.73 (m, 1H), 4.11-4.08 (t, J=6.4 Hz, 2H), 3.82 (s, 3H), 3.58-3.55 (t, J=6.4 Hz, 2H), 3.52-3.43 (m, 4H), 3.34 (s, 3H), 2.65 (m, 1H), 2.36 (m, 1H), 2.11-2.05 (m, 3H), 1.88 (m, 1H), 1.65 (m, 5H), 1.43 (s, 9H), 1.21 (s, 7H), 0.92 (m, 6H), 0.81 (m, 6H) ppm.

[Step 2]: Preparation of Aliskiren.

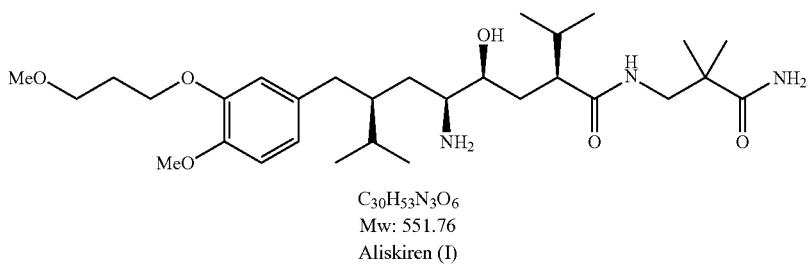 [SMILES: COCCCOc1cc(C[C@@H](C[C@H](N)[C@@H](O)C[C@H](C(=O)NCC(C)(C)C(N)=O)C(C)C)C(C)C)ccc1OC]

$C_{30}H_{53}N_3O_6$
Mw: 551.76
Aliskiren (I)

Under nitrogen protection, methylene chloride (40 ml) and trifluoroacetic acid (10 ml) are added into a 100 ml reaction bottle and the reaction mixture is cooled down to −15° C. with ice-salt bath under stirring, (1S,2S,4 S)-4-(2-carbamoyl-2-methylpropyl-carbamoyl)-2-hydroxy-1-{(S)-2-[4-methoxy-3-(3-methoxypropoxy)-benzyl]-3 methylbutyl}-5-methylhexyl)-carbamic acid tert-butyl ester (the compound of formula XXIII-A) (6.5 g, 10 mmol) is added in one batch and the reaction is maintained until TLC monitoring indicates the starting materials are almost completely exhausted. The reaction mixture is then neutralized with sorb urn hydroxide water solution (1 mol/L) with reaction temperature maintained below 0° C. The organic phase is collected and the remained, water phase is extracted with isopropyl ether (30 ml) for 3 times. All organic phases are combined and washed sequentially with saturated saline (30 ml), deionized water (30 ml) and dried with anhydrous sodium sulfate. After filtration and removal of solvent under reduced pressure, the residue is purified with short column of silica gel chromatography to obtain the Aliskiren compound of formula (I) (4.4 g) as a wax material. The yield is 75% as calculated from the compound of formula XXIII-A. The Aliskiren compound of formula I can be characterized by data collected from: MS m/z: 552.6 (M+H)$^+$; 1H-NMR (400 MHz, CDCl$_3$) δ 6.88-6.75 (m, 3H), 4.08-4.04 (t, J=6.3 Hz, 2H), 3.79 (s, 3H), 3.60-3.55 (t, 6.3 Hz, 2H), 3.30 (s, 3H), 3.30-3.25 (m, 3H), 2.69 (m, 2H), 2.49 (m, 1H), 2.27 (m, 1H), 2.04 (m, 2H), 1.78-1.35 (m, 7H), 1.10 (m, 6H), 0.90 (m, 12H) ppm.

Example 5

Preparation of Aliskiren

The same synthetic method in Example 4 is followed with the exception of concentrated sulfuric acid to replace the trifluoroacetic acid and −25° C. of reaction temperature in [Step 2].

Example 6

Preparation of Aliskiren

[Step 1] Preparation of (1S,2S,4S)-4-(2-carbamoyl-2-methylpropyl-carbamoyl)-2-hydroxy-1-{(S)-2-[4-methoxy-3-(3-methoxypropoxy)-benzyl]-3-methylbutyl}-5-methylhexyl)-carbamic acid benzyl ester (XXIII-B):

Under nitrogen protection, {(1S,3S)-1-((2S,4S)-4-isopropyl-5-oxo-furanidin-2-yl)-3-[4-methoxy-3-(3-methoxy-propoxy)-benzyl]-4-methyl-pentyl]-carbamic acid benzyl ester (the compound of formula XV-B) (5.7 g, 10 mmol), 2-hydroxypyridine (4.8 g, 5 mmol), toluene (20 ml) and triethylamine (10 ml) are sequentially added into a 50 ml reaction bottle and dissolved under stirring. 3-amino-2,2-dimethyl-propionamide (the compound of formula VII) (2.1 g, 18 mmol) is added and the reaction is heated up to reflux for 16 hours. After TLC monitoring demonstrates the starting materials are almost completely exhausted, the volume of the reaction mixture is minimized by distillation under reduced pressure. The resulted residue is cooled down and re-dissolved in ethyl acetate (100 ml) and then sequentially washed with saturated saline (30 ml), deionized water (30 ml) and dried with anhydrous sodium sulfate. After filtration and removal of solvent under reduced pressure, the residue is purified with short column of silica gel chromatography to obtain the compound of formula XXIII-B (5.6 g) as a wax material. The yield is 82% as calculated from the compound of formula XV-B. The compound of formula XXIII-B can be characterized by data collected from: MS m/z: 686.1 (M+H)$^+$; 1H-NMR (400 MHz, CDCl$_3$) δ 7.25-7.14 (m, 5H), 6.85-6.76 (m, 3H), 6.41 (brs, 1H), 6.23 (brs, 1H), 5.78 (brs, 1H), 5.41 (m, 1H), 5.23 (m, 1H), 4.79 (m, 1H), 4.13-4.10 (t, J=6.1 Hz, 2H), 3.90 (s, 3H), 3.61-3.57 (t, J=6.1 Hz, 2H), 3.57 (s, 3H), 3.52-3.43 (m, 4H), 2.65 (m, 1H), 2.35 (m, 1H), 2.25-2.05 (m, 3H), 1.96 (m, 1H), 1.77-1.70 (m, 2H), 1.68-1.59 (m, 2H), 1.41 (m, 1H) (m, 1H), 1.30 (s, 6H), 0.91 (m, 6H), 0.83 (m, 6H) ppm.

[Step 2] Preparation of Aliskiren.

In a hydrogenation kettle, (1S,2S,4S)-4-(2-carbamoyl-2-methylpropyl-carbamoyl)-2-hydroxy-1-{(S)-2-[4-methoxy-3-(3-methoxypropoxy)-benzyl]-3-methyl butyl}-5-methylhexyl)-carbamic acid benzyl ester (the compound of formula XXIII-B) (6.8 g, 10 mmol) is dissolved in methyl tert-butyl ether (100 ml) along with 5% Pd—C (0.5 g) and the hydrogenation is taken place under 25° C. and 3 atm for 16 hours until the TLC monitoring demonstrates the starting materials are exhausted. The reaction solution is filtered and catalyst is washed with methyl tert-butyl ether (50 ml). The filtrates are combined and solvent is removed under reduced pressure. The residue is purified with short column of silica gel chromatography to obtain Aliskiren (I) (4.8 g) as a wax material.

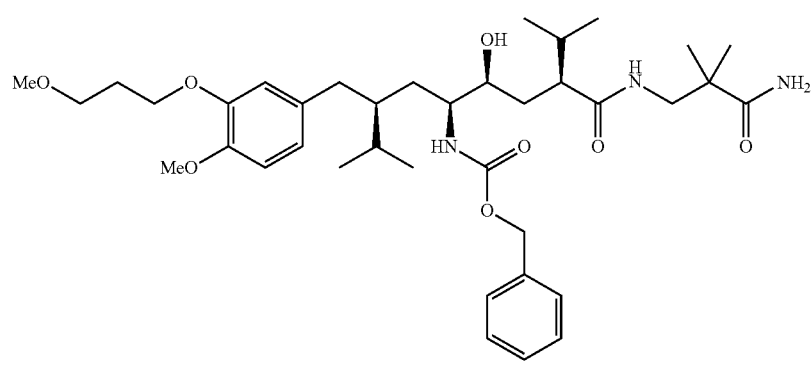

XXIII-B $C_{38}H_{59}N_3O_8$
Mol. Wt: 685.89

The yield is 86% as calculated from the compound of formula XXIII-B. The resulted product has analytic data agree with the product obtained in Example 4.

The embodiments described above are preferred embodiments of the present invention, and it should not be construed that the presentation is limited to the forms and contents of these particular embodiments. Those skilled in the art may resort to the scope of the invention with various changes, modifications or alterations without departing from the spirit and scope of the invention and should be considered as equivalent embodiments in the scope of the invention. Also, it should be understood that these practices with various changes, modifications or alterations without departing from the spirit and scope of the invention should be considered within the scope of the present invention.

The invention claimed is:

1. A method for preparing the Aliskiren intermediate compound of formula XV comprising the steps of

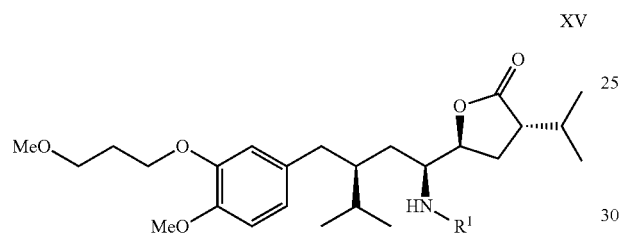

XV (1). reacting the compound of formula IX
4-bromo-1-methoxy-2-(3-methoxypropoxy)benzene with sequentially added isopropylmagnesium chloride and n-butyllithium in an ether class solvent under temperature of −25° C.-20° C. to obtain the intermediate compound of formula XXII;

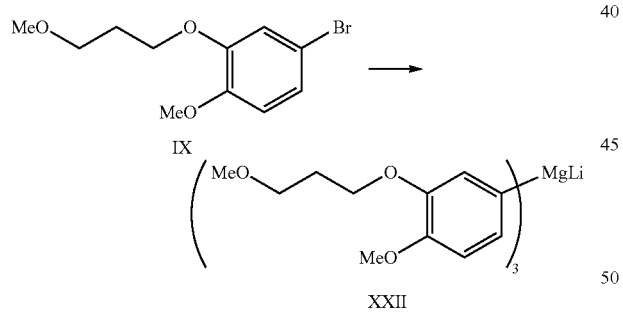

(2). methylsulfonylation of the compound of formula XIX in an inert. solvent under temperature of −10° C.-25° C. to obtain the compound of formula XX.

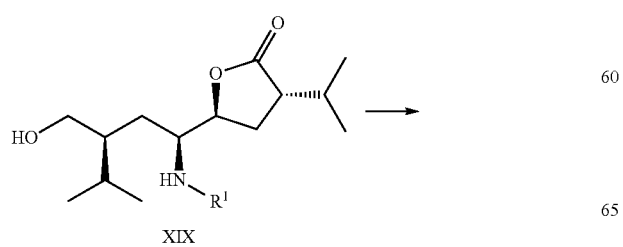

XIX

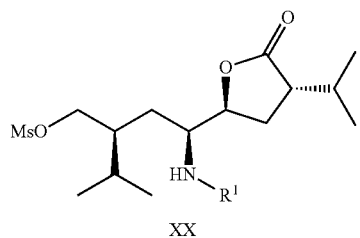

XX wherein Ms is methylsulfonyl group.

(3). substituting the intermediate compound of formula XX with anhydrous lithium bromide in a ketone class solvent under temperature of 35° C. to refluxing temperature to obtain the intermediate compound of formula XXI;

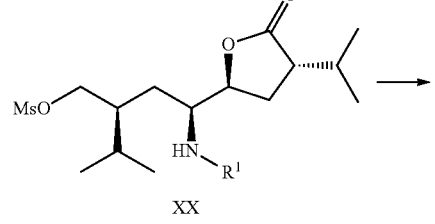

XX

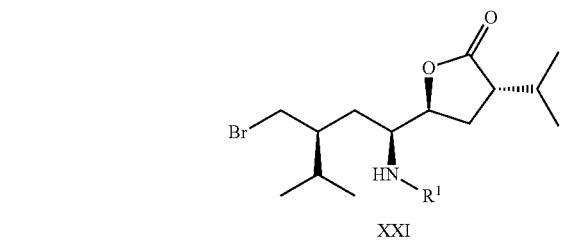

XXI (4). coupling the intermediate compound of formula XXII in step (1) with the intermediate compound of formula XXI in step (3) in an ether class solvent under temperature of −25° C.-55° C. with the presence of iron-contained catalyst to obtain the compound of formula XV;

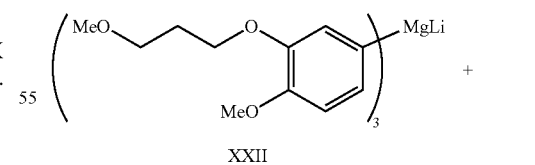

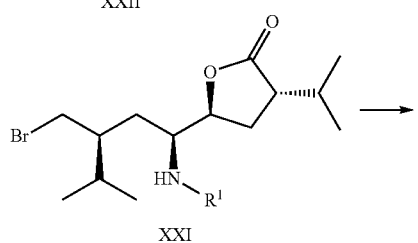

XXI

-continued

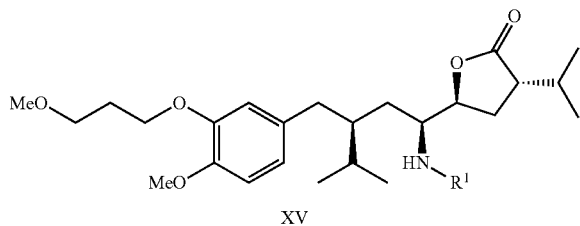

wherein R¹ is *tert*butoxycarbonyl or benzyloxycarbonyl group in the compounds of formula XV, XIX, XX and XXI in the above reaction steps.

2. The method according to claim 1 wherein the ether class solvent in step (1) is one selected from diethyl ether, tetrahydrofuran or 1,2-dimethoxyethane.

3. The method according to claim 1 wherein the inert solvent in step (2) is methylene chloride or tetrahydrofuran.

4. The method according to claim 1 wherein the ketone class solvent in step (3) is acetone or 2-butanone; and the molar ratio between lithium bromide and the compound of formula XX 1.1 to 5.

5. The method according to claim 1 wherein the said ether class solvent in step (4) is either one or mixture of any two selected from diethyl ether, tetrahydrofuran or 1,2-dimethoxyethane; the said iron-contained catalyst is selected from iron(III) acetylacetonate or Iron(III) chloride; and the reaction temperature is 15° C.~20° C.

6. A method for preparing the Aliskiren intermediate compound of formula I according to claim 1, the method for preparing the Aliskiren intermediate compound of formula I further comprising the steps of:

(a). preparing the compound of formula XXIII from the compounds of formula XV and VII according to claim 1 in the presence of 2-hydroxypyridine and triethylamine;

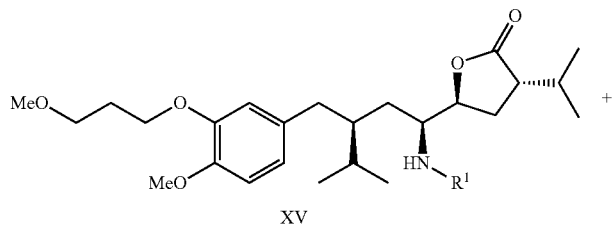

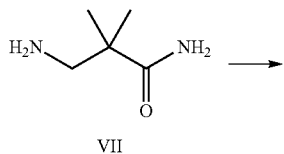

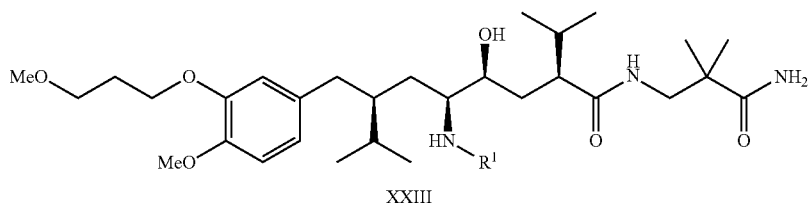

(b). removing R¹ on the amino group of the compound of formula XXIII to obtain the Aliskiren compound of formula I;

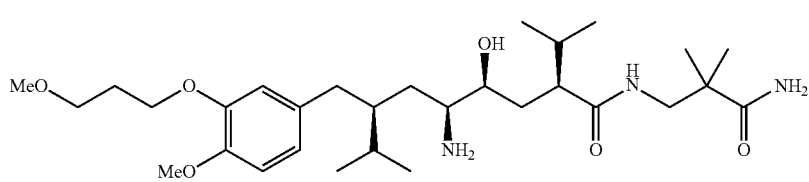

wherein the R$^1$ is $^{tert}$butoxycarbonyl or benzyloxycarbonyl group in the compounds of formula XV and XXIII.

7. The method according to claim 6 for preparing the Aliskiren compound of formula I, wherein the reaction in step (a) between the compound of formula XV and the compound of formula VII to obtain the compound of formula XXIII is implemented in an inert solvent.

8. The method according to claim 7 for preparing the Aliskiren compound of formula I, wherein the inert solvent is one selected from dioxane or toluene.

9. The method according to claim 6 for preparing the Aliskiren compound of formula I, wherein the acidic de-alkylation to remove group is performed under −25° C.-0° C. with the acid is one selected from trifluoroacetic acid, hydrochloride and concentrated sulfuric acid when said R$^1$ is $^{tert}$-butoxycarbonyl group.

10. The method according to claim 6 for preparing the Aliskiren compound of formula I, wherein the catalytic hydrogenation to remove R$^1$ group is performed in the presence of Pd—C catalyst under 20° C.-60° C. and 1 to 10 atm when said R$^1$ is benzyloxycarbonyl group.

11. The method according to claim 6 wherein the ether class solvent in step (1) is one selected from diethyl ether, tetrahydrofuran or 1,2-dimethoxyethane.

12. The method according to claim 6 wherein the inert solvent in step (2) is methylene chloride or tetrahydrofuran.

13. The method according to claim 6 wherein the ketone class solvent in step (3) is acetone or 2-butanone; and the molar ratio between lithium bromide and the compound of formula XX is 1.1 to 5.

14. The method according to claim 6 wherein the said ether class solvent in step (4) is either one or mixture of any two selected from diethyl ether, tetrahydrofuran or 1,2-dimethoxyethane; the said iron-contained catalyst is selected from iron(III) acetylacetonate or iron(III) chloride; and the reaction temperature is −15° C.~20° C.

* * * * *